(12) United States Patent
Johnson et al.

(10) Patent No.: US 8,656,760 B2
(45) Date of Patent: Feb. 25, 2014

(54) IMPACT PENETROMETER SYSTEMS FOR CHARACTERIZING SOIL PROPERTIES

(75) Inventors: Jerome Johnson, Fairbanks, AK (US); Kris Zacny, New York, NY (US); Philip Chu, Houston, TX (US)

(73) Assignee: Honeybee Robotics, Ltd., New York, NY (US)

( * ) Notice: Subject to any disclaimer, the term of this patent is extended or adjusted under 35 U.S.C. 154(b) by 331 days.

(21) Appl. No.: 13/229,885

(22) Filed: Sep. 12, 2011

(65) Prior Publication Data
US 2012/0174659 A1  Jul. 12, 2012

Related U.S. Application Data

(60) Provisional application No. 61/383,992, filed on Sep. 17, 2010.

(51) Int. Cl.
*G01N 3/00* (2006.01)

(52) U.S. Cl.
USPC .................................................. 73/85; 73/84

(58) Field of Classification Search
USPC ................................ 73/78, 81, 82, 83, 84, 85
See application file for complete search history.

(56) References Cited

U.S. PATENT DOCUMENTS

| | | | | |
|---|---|---|---|---|
| 4,492,111 A | * | 1/1985 | Kirkland | 73/84 |
| 4,858,935 A | * | 8/1989 | Capson | 473/570 |
| 5,493,895 A | * | 2/1996 | Cyr et al. | 73/12.13 |

* cited by examiner

*Primary Examiner* — David Z Huang
(74) *Attorney, Agent, or Firm* — Leighton K. Chong

(57) ABSTRACT

A dual aerial-drop penetrometer system includes a high-velocity (>30 m/s) penetrometer aerial unit combined with a low-velocity (<10 m/s) penetrometer aerial unit. The primary penetrometer is formed as an outer shell having the secondary penetrometer received in telescoping fashion within, which is ejected by a spring ejection mechanism upon impact of the outer shell. Both penetrometers provide deceleration information as they penetrate the soil of interest. The data from the two penetrometers, after analysis, can be used to assess soil strength as well as trafficability for the deployment of remotely-controlled vehicles, for example.

20 Claims, 9 Drawing Sheets

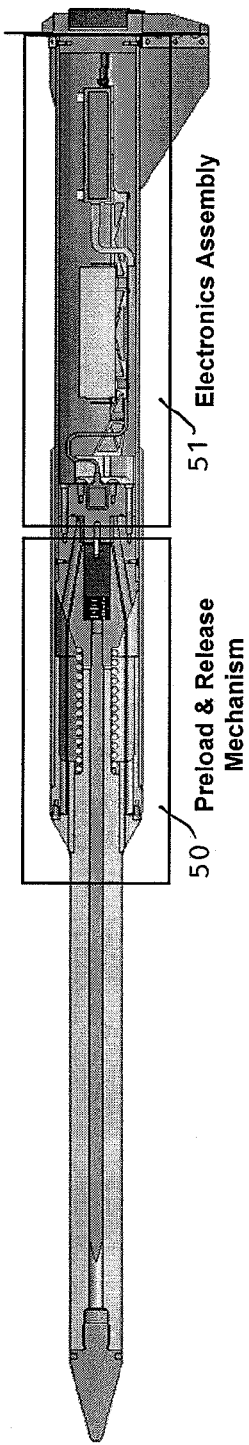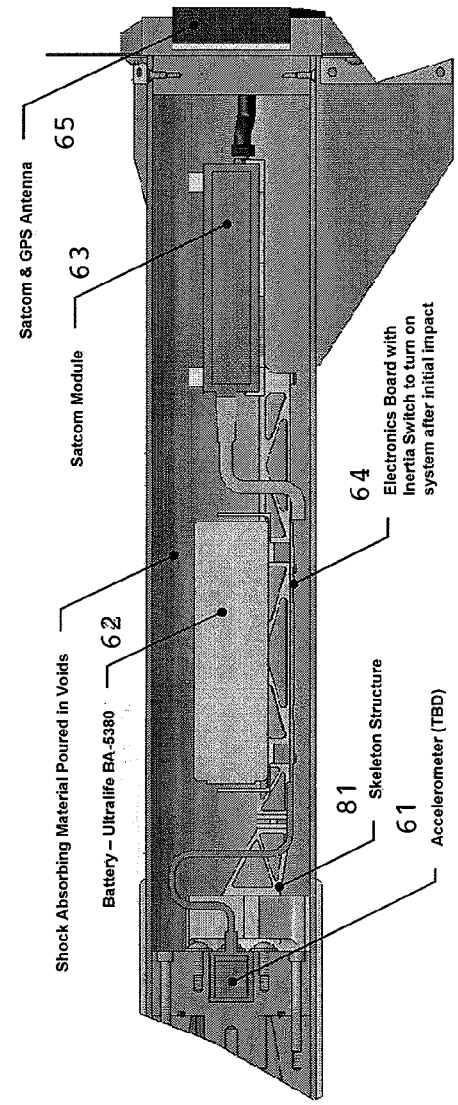
Figure 5
Figure 6

1. Just Prior to Impact – Penetrometer Locked

Figure 9A

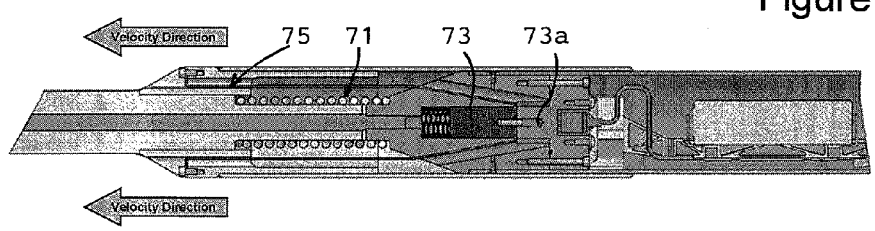

2. Just After Impact – Release Slug propelled downwards. Dowel pin no longer in contact with restraint cable loops. Restraint cable loops begin to release hold on penetrometer

Figure 9B

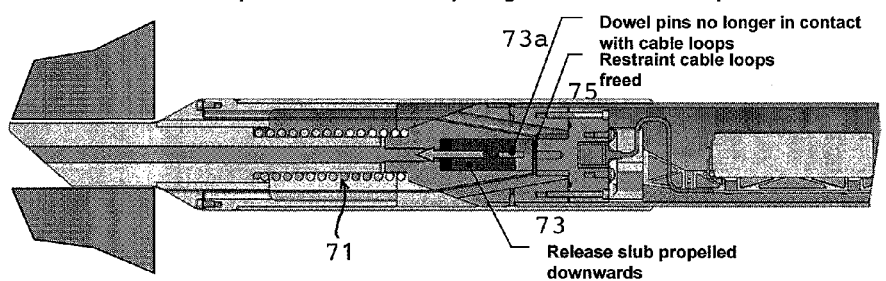

3. After Impact – Heavy spring preload starts to eject penetrometer from Outer Shell. Cable loops freed from Penetrometer

Figure 9C

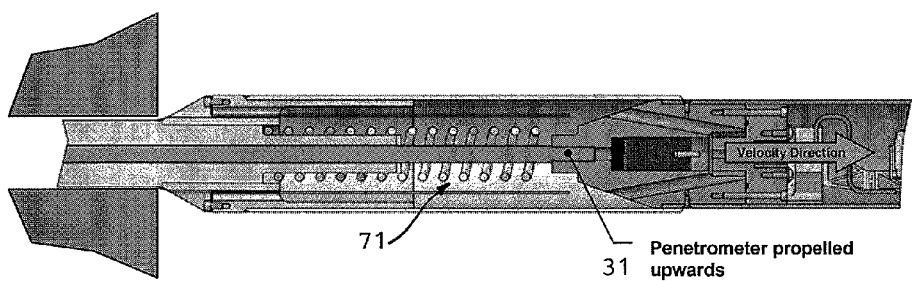

4. After Impact – Penetrometer completely clear of Outer Shell components

Figure 9D

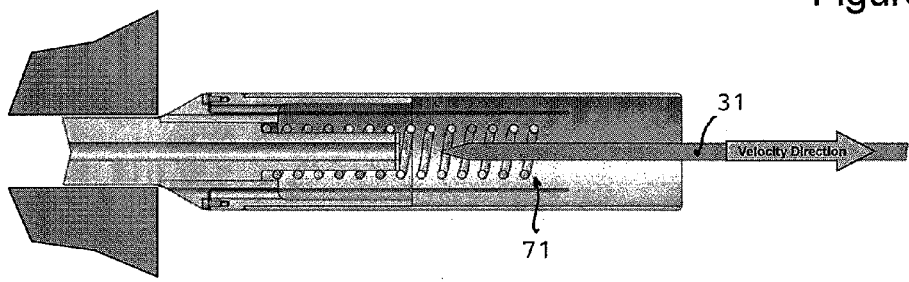

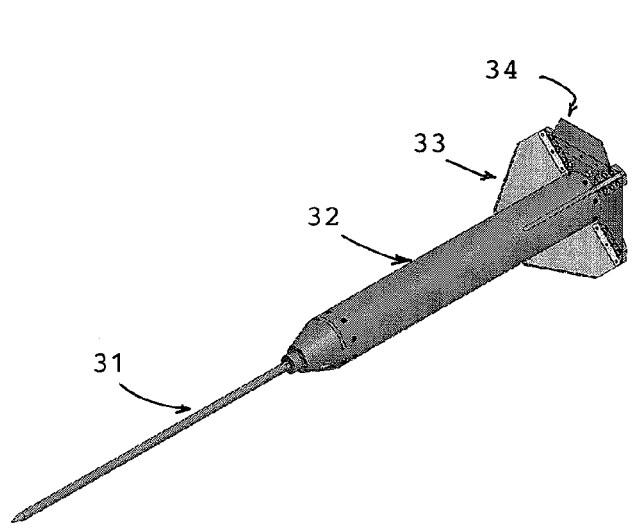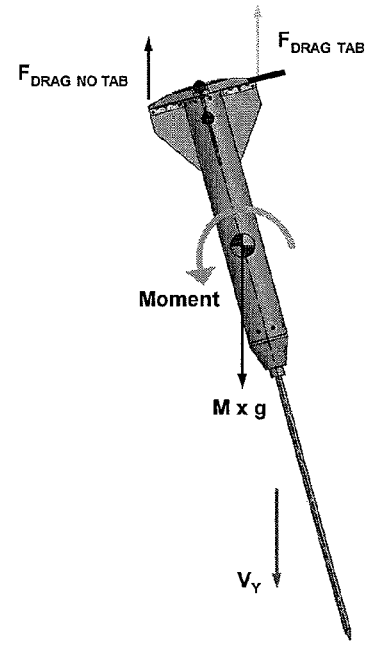
Figure 10A                 Figure 10B
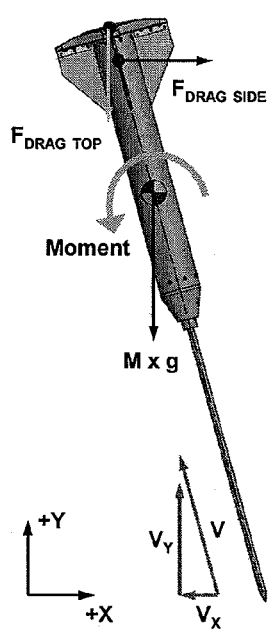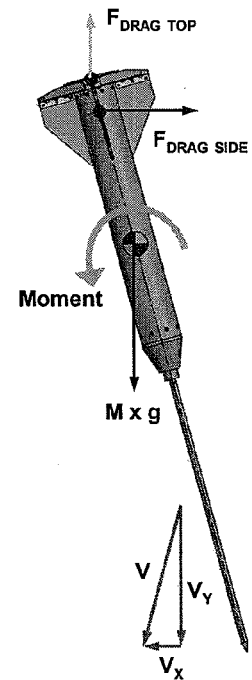
Figure 10C                 Figure 10D

IMPACT PENETROMETER SYSTEMS FOR CHARACTERIZING SOIL PROPERTIES

This U.S. patent application claims the priority filing date of U.S. Provisional Application No. 61/383,992, filed on Sep. 17, 2010, entitled "Impact Penetrometer Systems for Characterizing Soil Properties".

The subject matter of this U.S. patent application was developed under a grant obtained through the Department of Defense SBIR Phase I program, Contract No. N0001409M0227, administered through the Office of Naval Research. The U.S. Government retains certain rights in the invention.

FIELD OF INVENTION

The present invention relates to a method and systems for to remotely determine soil strength and trafficability, and particularly to aerial drop penetrometer systems.

BACKGROUND OF INVENTION

Prior aerial drop penetrometers achieved uncontrolled high velocities during impact or required parachutes to slow their decent. High velocity impact resulted in penetrometer deceleration that was primarily caused by soil inertia, not soil strength. Soil inertia is a function of soil density while soil strength determines soil trafficability and foundation support properties. Parachute dropped penetrometers tended to drift off target and may not impact vertically. An uncontrolled high velocity penetrometer (as used in the prior art) will decelerate upon impact with soil primarily as a result of soil inertia (density) with only a slight affect due to soil strength thereby only providing crude knowledge of the soil strength.

For an aerial-dropped penetrometer that impacts soil, the factors that cause its deceleration include soil strength, friction between the soil and penetrometer surface, and soil inertia (acceleration of the soil mass by the penetrometer). Where reduced complexity is important and soil strength is the parameter of interest, the single most important sensor for an aerial-dropped penetrometer is an accelerometer, which measures the deceleration of the penetrometer upon impact in the soil. Penetrometer deceleration factors can be assessed in terms of friction, strength and inertia using a physical model of penetration impact. In some cases, penetrometer data can be interpreted to determine soil type (when impact velocity is relatively low or both high velocity and low velocity impact velocity is available). At higher impact velocities, both the effects of strain rate (for cohesive soils) and inertia need to be considered.

Soil type can generally be categorized as granular (e.g., sand) or cohesive (e.g., clay). Granular soils obtain their strength through frictional contacts between soil grains that produce an increasing strength with depth as the weight of soil overburden increases. For granular soils, penetrometer deceleration will increase with depth of penetration. Cohesive soils gain their strength primarily through electrical bond attraction between fine soil particles that results in a relatively constant strength throughout the layer of similar soil type. For cohesive soils, penetrometer deceleration will generally remain constant with penetration depth. Friction effects will be present but are generally small for cohesive soils and larger for granular soils. The unique character of penetrometer deceleration in granular and cohesive soils allows them to be identified through the measured penetrometer deceleration.

When the penetrometer impact velocity exceeds 30 m/s, the deceleration process is dominated by inertia for both granular and cohesive soils. At such high impact velocities, it becomes difficult, if not impossible, to identify the soil type from the penetrometer deceleration data. If there are no alternate means (e.g., remote sensing data) to identify soil type in the inertia driven regime, then it is necessary to estimate strength values (one value for granular soil and a second value for cohesive soil) using an analysis method that can separate the effects of inertia, friction, and strength. Since the strength magnitude will be for the deformation rate imposed by the high-velocity impact, it is necessary to correct the strength magnitude for rate effects, then a rate-corrected Cone Index measure (CI) can be estimated using a correlation to soil strength. If soil type can be identified using remote sensing data or by the addition of another sensor to the penetrometer, such as a pore pressure sensor, then the strength value for the identified soil can be calculated directly, using a method that accounts for inertia, friction, and strength.

At low-velocity impacts, inertia will still affect the deceleration process, but at a much reduced amount in comparison to friction and soil strength mechanisms. In this case, soil type can be identified as granular or cohesive directly from analysis of the penetrometer deceleration data. The association of penetrometer deceleration to soil strength has the possibility of being determined through direct correlation or the use of semi-physical models (to improve accuracy). Once strength is estimated it needs to be corrected for rate effects and then correlated with CI and/or CBR (California Bearing Ratio) for use in a vehicle mobility model. In order to decrease penetrometer velocity to ~8 m/s, a number of methods can be employed, including deployable parachutes, but these have the disadvantage of being strongly affected by wind.

SUMMARY OF INVENTION

In accordance with the present invention, a dual aerial-drop penetrometer system includes a high-velocity (>30 m/s) penetrometer aerial unit combined with a low-velocity (<10 m/s) penetrometer aerial unit. Both penetrometers provide deceleration information as they penetrate the soil of interest. The data from the two penetrometers, after analysis, can be used to assess soil strength as well as trafficability for the deployment of remotely-controlled vehicles, for example.

The 'two' penetrometer combination gathering high-velocity and low-velocity impact data in a single package provides the most robust, accurate, and least risky approach to characterizing soil properties remotely. This unique approach to impact penetrometer design takes advantage of knowledge of both soil inertia and strength to maximize information about the soil.

In a preferred embodiment of the combination penetrometer system, the low-velocity penetrometer system containing a global positioning satellite sensor (GPS), a satellite communications module (SatComm), and an accelerometer is inserted into a detachable outer shell. The high-velocity penetrometer system provides the outer shell and contains the low-velocity penetrometer system within. The penetrometer combination in the outer shell can be deployed from the unmanned aerial vehicle (UAV). Descent speed is controlled by passive drag features on the combination system in the outer shell. The outer shell will impact the soil at a high velocity and become partially buried. Immediately following impact, the inner penetrometer system is released and propelled, for example, by a spring, from an upper side of the outer shell to a specified height, which is determined by the spring constant and degree of compression. It will then fall to the ground, impacting the soil surface at a desired low impact velocity of about 8 m/s, thereby penetrating the soil to a minimum of 0.5 meters. A small trim tab incorporated into the primary penetrometer design provides a drag feature that ensures a small degree angle of inclination so that the secondary impact occurs >1 m away from the primary impact. For a small angle of 5° or less, the error associated with deceleration and depth measurements due to the inclination angle is less than 0.5%.

The deceleration data from both the high-velocity and low-velocity impacts can be packetized and transmitted to a base of operations using a satellite communications module built into the penetrometer systems. Onboard data processing and instantaneous go/no-go decision making is not required but can be implemented if the requirements change. The high-velocity (>30 m/s) penetrometer impact data will provide crude knowledge of the soil strength but will provide information about soil density, while the low-velocity (<10 m/s) penetrometer impact data will provide much more accurate knowledge of soil strength. The dual systems approach substantially reduces overall system risk associated with target accuracy, system design complexity, and accurate interpretation of deceleration measurements. The first high speed impact is relatively simple and thus less risky, but at the same time offers lower fidelity soil measurements. The soil data from the secondary, low-velocity impact, which is contingent on successful spring deployment of the secondary penetrometer from the shell, carries more risk, but if successful, offers high fidelity soil data. The combined system can be integrated with other sensors (e.g. moisture sensor, pore pressure sensor) to acquire higher fidelity data of a soil site.

Other objects, features, and advantages of the present invention will be explained in the following detailed description of the invention having reference to the appended drawing.

BRIEF DESCRIPTION OF DRAWINGS

FIG. 5 shows an electronics assembly and preload and release mechanism assembly for the combined penetrometer unit.

FIG. 6 shows the electronics assembly in detail.

FIGS. 9A-9D illustrate a method of locking the secondary penetrometer in place and releasing it by spring ejection upon impact of the outer shell against the ground.

FIGS. 10A-10D illustrate the use of trim tab features to control the fall of the outer shell under gravity and tilt angle to allow clearance of the secondary penetrometer upon ejection from the buried outer shell.

DETAILED DESCRIPTION OF INVENTION

In the following detailed description of the invention, certain preferred embodiments are illustrated providing certain specific details of their implementation. However, it will be recognized by one skilled in the art that many other variations and modifications may be made given the disclosed principles of the invention.

In accordance with the present invention, a dual aerial-drop penetrometer system includes a high speed (>30 m/s) penetrometer aerial unit combined with a low speed (<10 m/s) penetrometer aerial unit. Both penetrometers provide deceleration information as they penetrate the soil of interest. The data from the two penetrometers, after analysis, can be used to assess soil strength as well as trafficability for the deployment of remotely-controlled vehicles, for example.

Figure 1:
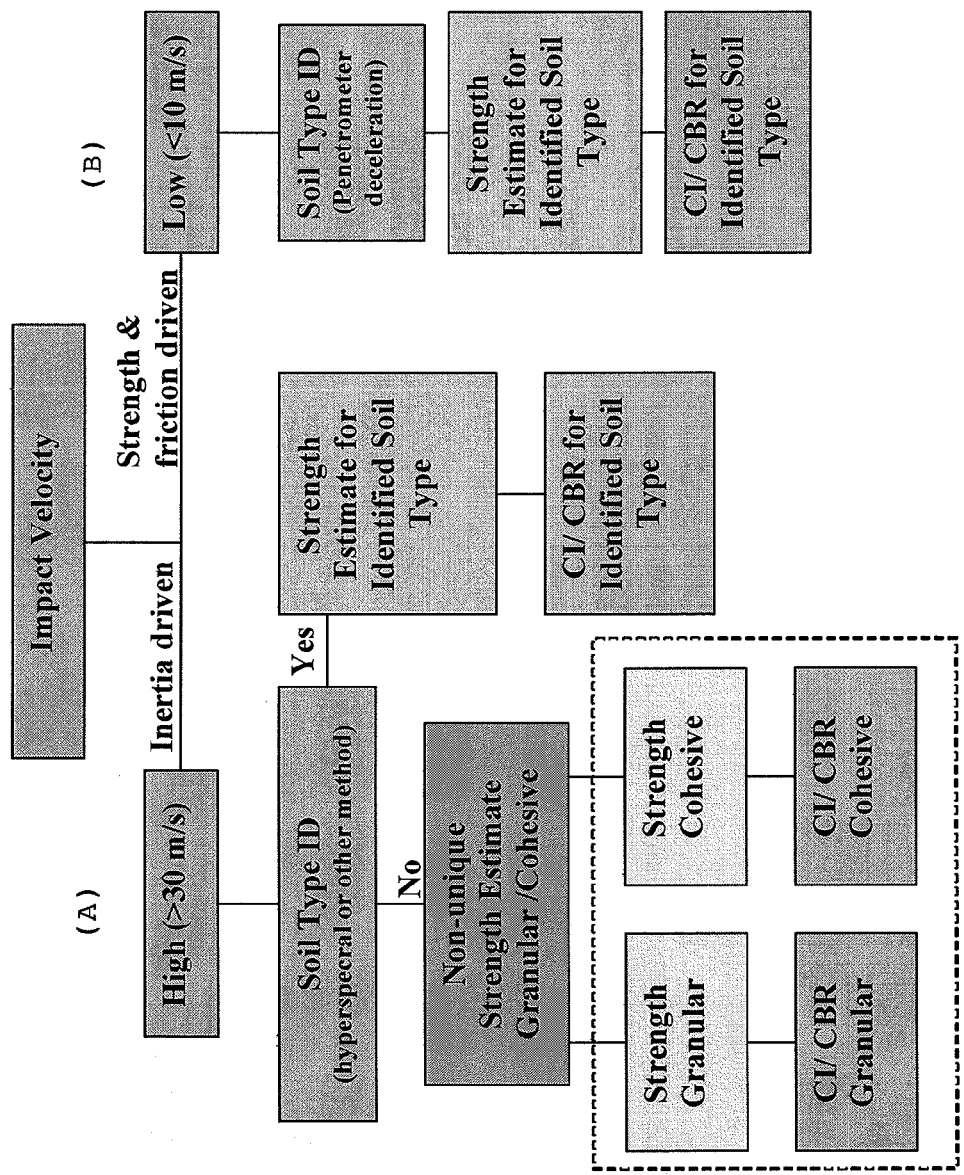
FIG. 1 shows a flow chart for deriving desired measures for soil properties from dual-impact, penetrometer deceleration data.

From an understanding of information to be determined from the dual-impact, penetrometer deceleration data, a decision tree analysis flow chart is shown in FIG. 1 to derive the desired measures for soil properties, such as strength, CI, and CBR, and possibly other soil properties. The CI (Cone Index) and CBR (California Bearing Ratio) measures are suitable index parameters for calculating the expected mobility of vehicles over the soil of interest using standard mobility models. The starting point of analysis is to first determine the penetrometer velocity at impact and during deceleration using accelerometer data.

For the high-velocity (>30 m/s) penetrometer impact (Column A), the deceleration process is dominated by inertia for both granular and cohesive soils, and the analysis flows down the left hand side of the chart. At such high impact velocities, it becomes difficult, if not impossible, to identify the soil type from the penetrometer deceleration data. If there are no alternate means to identify soil type in the inertia driven regime, then it is necessary to follow the "non-unique" path of the analysis chart and estimate two strength values (one value for granular soil and a second value for cohesive soil (shown within the dashed box on the lower left hand side of the chart) using an analysis method that can separate the effects of inertia, friction, and strength. Since the strength magnitude will be for the deformation rate imposed by the high-velocity impact, it is necessary to correct the strength for rate effects using a method known in the industry, and then Cone Index CI/CBR measures can be estimated for Strength Granular and Strength Cohesive using a standard correlation to soil strength. If soil type can be identified using remote sensing data or by the addition of another sensor to the penetrometer, such as a pore pressure sensor, then the strength value for the identified soil can be calculated directly, again using a method that accounts for inertia, friction, and strength.

For the low-velocity (<10 m/s) penetrometer impact (Column B), inertia will still affect the deceleration process, but at a much reduced amount in comparison to friction and soil strength mechanisms, and the analysis is indicated down the right hand side of the chart. In this case, soil type can be identified as granular or cohesive directly from analysis of the low-velocity penetrometer deceleration data. The association of penetrometer deceleration to soil strength has the possibility of being determined through direct correlation or the use of semi-physical models (to improve accuracy). Once strength is estimated, it can be corrected for rate effects and then correlated with CI and/or CBR for use in a mobility model. The two important conclusions to be drawn from the flow chart analysis approach are that some useful information about soils strength can be determined from the high-velocity penetrometer impact and quite good accuracy can be achieved from the low-velocity impact.

The dual-impact penetrometer combination gathering high-velocity and low-velocity impact data in a single package provides the most robust, accurate, and least risky approach to characterizing soil properties remotely. This unique approach to impact penetrometer design takes advantage of knowledge of both soil inertia and strength to maximize information about the soil.

Upon evaluation of a number of deployment options, a preferred architecture for the dual-impact penetrometer system balancing parameters such as simplicity, cost, science return, reliability, targeting accuracy and low visibility of operation was determined to be an aerial-drop of the combined units in an outer-shell for a primary penetrometer for the high-velocity impact and secondary deployment of a spring-ejected secondary penetrometer for the low-velocity impact.

Figure 2:
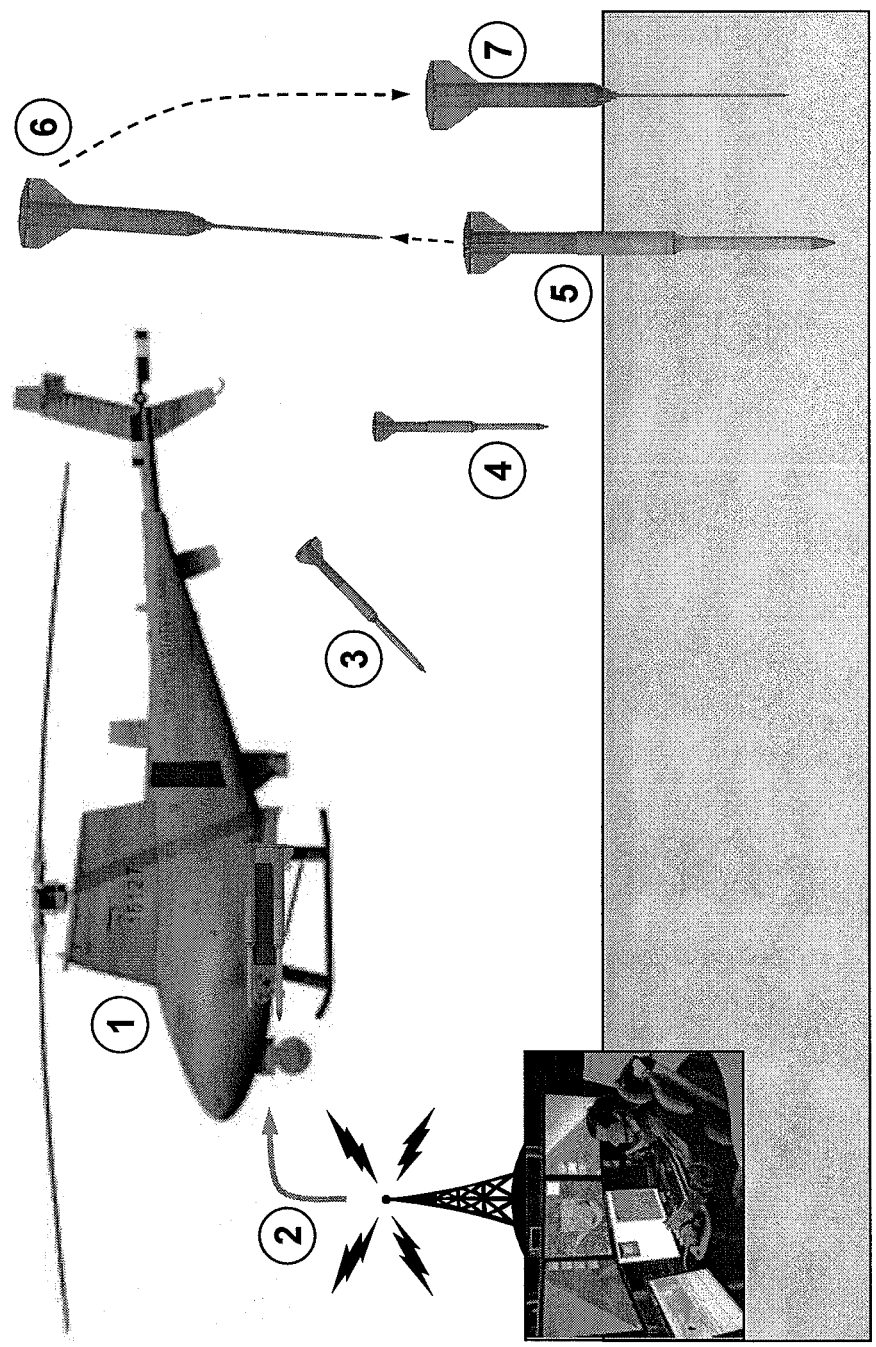
FIG. 2 illustrates a likely dual-impact penetrometer deployment scenario.

FIG. 2 illustrates a likely dual-impact penetrometer deployment scenario. The combined unit is dropped from an aerial vehicle such as an unmanned aerial vehicle 1 upon receiving a command signal from a control unit 2. The combined unit in outer shell 3 accelerates in free fall (indicated at numeral 4) and impacts the soil together (indicated at numeral 5). A drop height greater than 50 m will result in terminal velocity on primary impact of greater than 30 m/s. The high-velocity impact generates high forces partially burying the outer shell into the ground. Immediately following the first impact, the secondary penetrometer 6 is ballistically ejected from the outer shell to a height of about 5 m or less above the ground, after which it descends in free fall and impacts the soil at a low velocity of about 10 m/s or less (indicated at numeral 7). A small trim tab in primary penetrometer drag angle ensures that the secondary penetrometer 6 is ejected at a slight angle and its secondary impact occurs a safe distance away (>1 m) from the primary impact. The error in deceleration and depth measurements due to the small trim tab angle (~5° is expected to be less than 0.5%.

During descent and after impact, a GPS receiver within the primary penetrometer may be used to establish a satellite fix and determines the unit's location. During initial impact, deceleration data is recorded to capture high-velocity impact information. Immediately following primary impact, the secondary penetrometer is ejected from the outer shell at an angle to a specific height above the ground in order to impact the surface at a known low velocity. The penetrometer electronics records deceleration data for the low-velocity impact, and can transmit the deceleration data and GPS coordinates to the receiving station. The data can then be processed at the receiving station to determine whether the area of interest is trafficable, such as for deployment of remote-controlled land vehicles and robotics.

Figure 3:
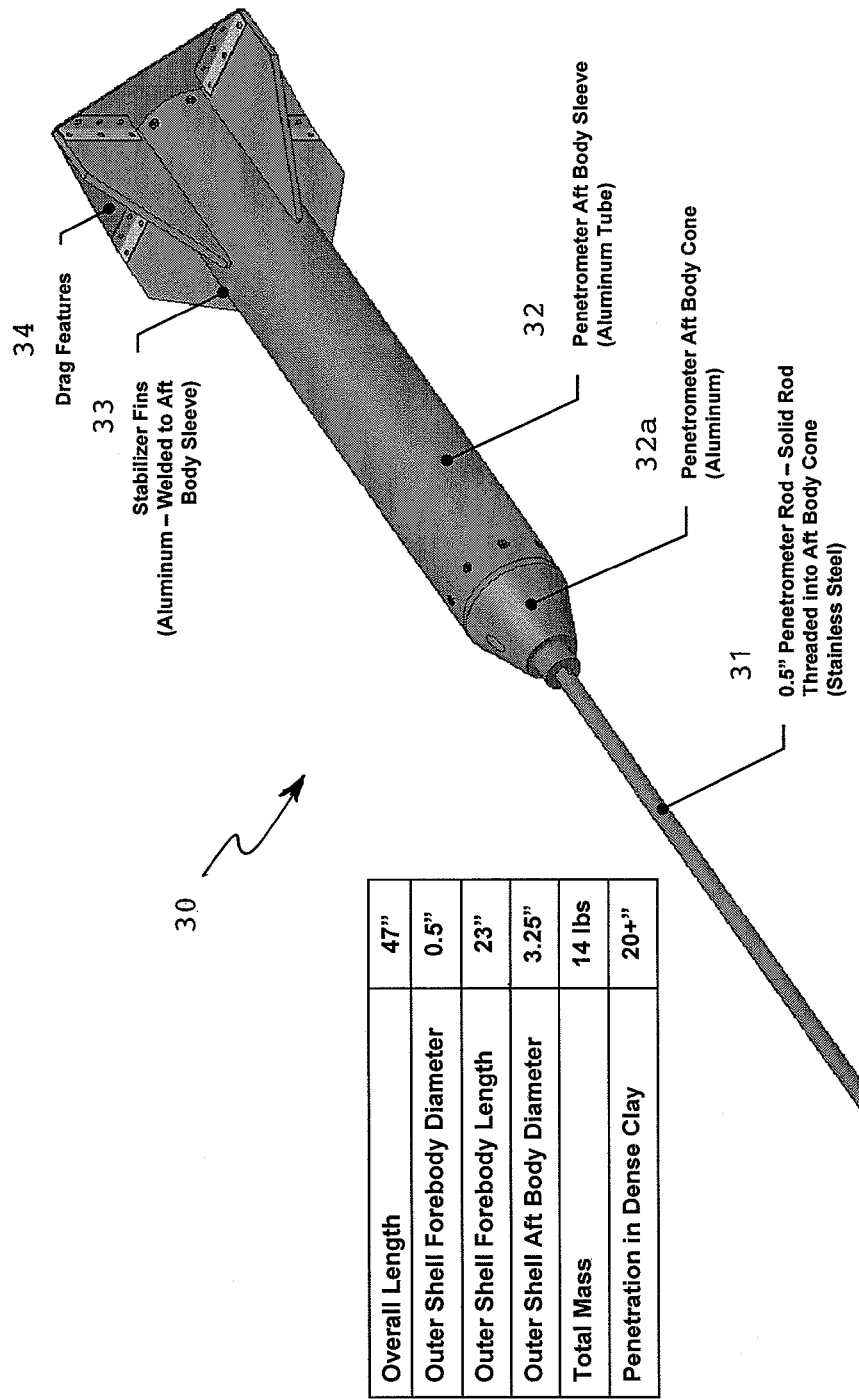
FIG. 3 illustrates a spring-ejected secondary penetrometer without an outer shell.

The preferred outer shell with inner spring-ejected penetrometer architecture offers a simple, low cost method of determining soil properties using a consistent, low velocity impact, without the need for parachutes and active drag features. FIG. 3 illustrates the spring-ejected secondary penetrometer without the outer shell. As shown, the secondary penetrometer 30 consists of a narrow (for example, 0.5" diameter) elongated fore body penetrometer rod 31 for achieving a desired amount of penetration into dense soils (for example, 15-20 inches, an aft body nose cone 32a, and a hollow cylindrical (for example, 3.25" diameter) aft body sleeve 32 for housing the penetrometer electronics. Stabilizer fins 33 are attached to the rear portion of the aft body sleeve 32 with drag features 34. The accompanying table in the Figure shows typical preferred physical parameters for the secondary penetrometer.

Figure 4:
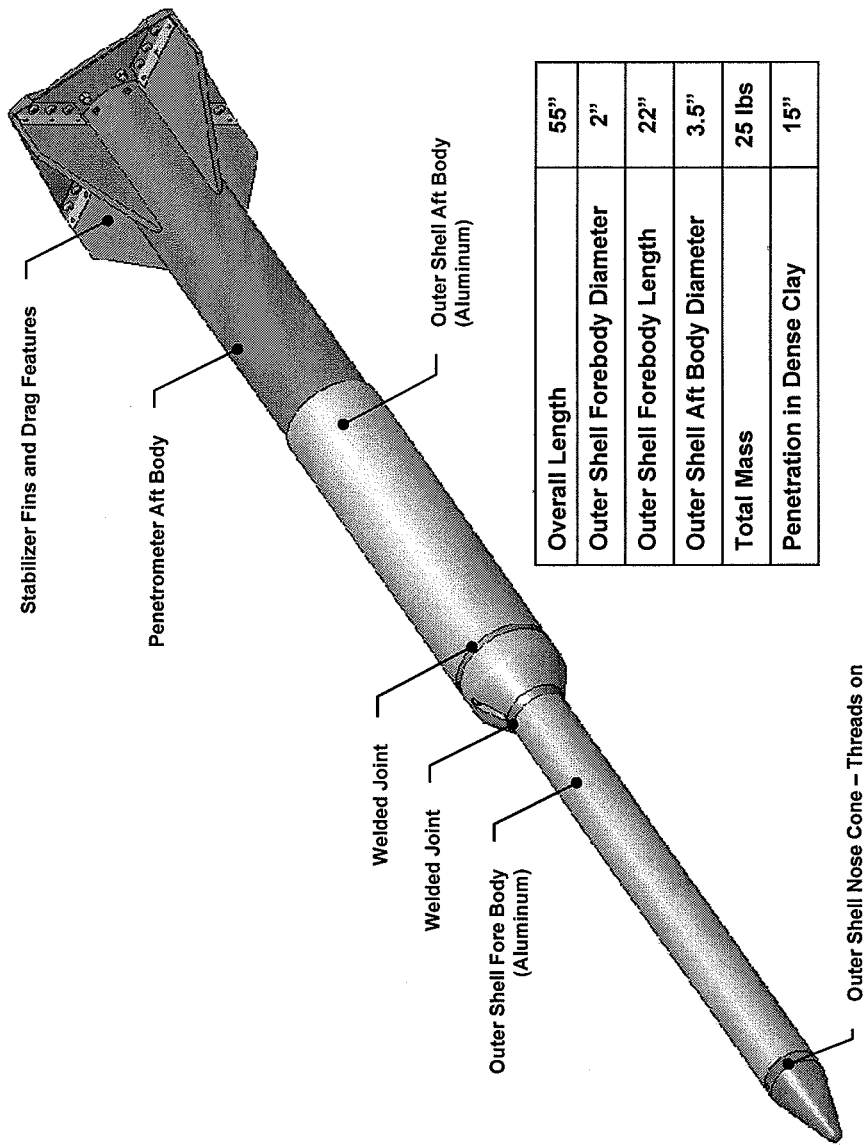
FIG. 4 illustrates the spring-ejected secondary penetrometer housed within an outer shell that houses a primary penetrometer.

FIG. 4 shows a primary penetrometer formed as an outer shell 40 having an outer shell nose cone 41, outer shell fore body 42, and outer shell aft body 43 which receives the fore body 31 and nose cone 32a of the secondary penetrometer in telescoping fashion within a rear recess formed therein. The secondary penetrometer nose cone is received in mating fashion in the rear recess of the outer shell aft body of the primary penetrometer. The secondary penetrometer aft body sleeve 32, stabilizer fins 33, and drag features 34 form the rear portion to the outer shell that controls the descent and angle of impact of the combined unit. The accompanying table in the Figure shows typical preferred physical parameters for the combined unit. For the preferred parameters given, it is expected that the outer shell will impact the surface at approximately 250 ft/s (82 m/s), and with its blunt nose cone penetrate at least 15 inches into a dense clay soil. As mentioned previously, the secondary penetrometer is ejected from the outer shell immediately following impact of the outer shell into the ground.

The integrated penetrometer and outer shell include two additional sub-assemblies, the electronics assembly 50 and the preload and release mechanism assembly 51, as shown in FIG. 5.

The electronics assembly is shown in detail in FIG. 6 having an accelerometer 61, battery 62, satellite/GPS communications module 63, electronics board 64 and satellite/GPS antenna 65 mounted in a skeleton structure 81 (described below).

Figure 7:
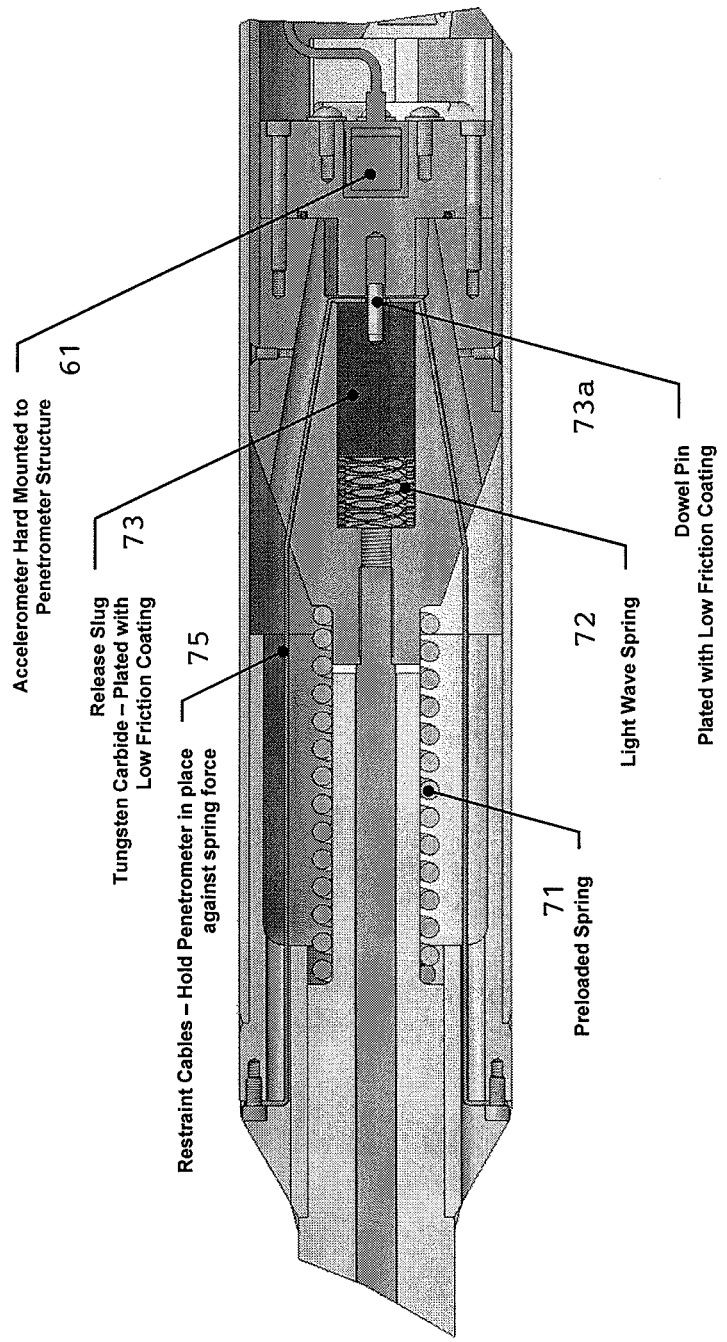
FIG. 7 shows the preload and release mechanism assembly in detail.

FIG. 7 shows the preload and release mechanism assembly in detail having a preloaded spring 71 for ejecting the secondary penetrometer, a light wave spring 72 for isolating impact forces on the electronics assembly, a release slug 73 and dowel pin 73s for the secondary penetrometer rod, an secondary penetrometer accelerometer 74, and restraint cables 75 to hold the secondary penetrometer in place against the spring force. The purpose of the release mechanism is to keep the spring preloaded penetrometer from ejecting prior to impact, and to enable the secondary penetrometer to eject during impact of the outer shell.

Figure 8:
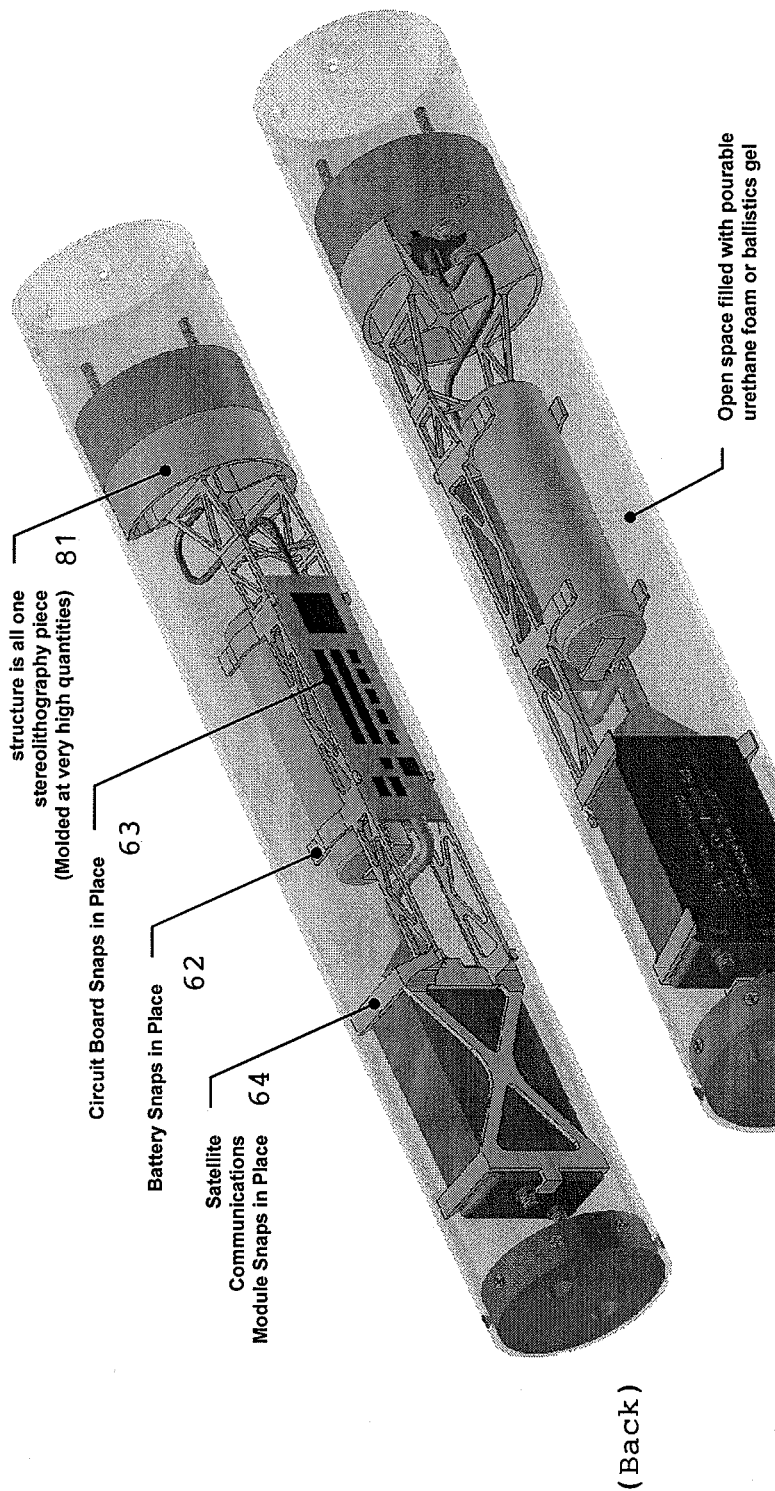
FIG. 8 illustrates (Front and Back views) the electronic components of the penetrometer unit mounted into a plastic skeleton structure.

As illustrated (Front and Back views) in FIG. 8, all of the shock-sensitive electronic components (Satellite Communications module 63, battery 62, and electronics board 64) can be first mounted into a plastic skeleton structure 81. This plastic structure may made using a stereolithography technique at low quantities, and may be injection molded at high quantities. The skeleton structure 81 can consist of flexible members to allow the satellite communications module, battery, and electronics board to snap in place. This would simplify assembly of these interior components, particularly at high production quantities. Once the electronic components are snapped in place, the entire skeleton structure is inserted into the penetrometer. In order to provide shock protection, urethane foam or ballistics gel may be poured into the assembly casing volume, filling all of the vacant cavities, effectively encasing each individual component in a protective, shock isolated padding once the material sets. The purpose of the skeleton structure is simply to hold all the components in position while the foam or gel is being poured. Although the penetrometer may experience the same impact shock as the outer shell, the foam or gel will protect the more sensitive electronic components from being damaged from the impact, and will insure that they function after impact.

During assembly of the secondary penetrometer and outer shell, the penetrometer is preloaded against a spring housed within the outer shell, then locked in place. FIGS. 9A-9D illustrates a novel and inexpensive method of locking the secondary penetrometer in place and releasing it by spring ejection upon impact of the outer shell against the ground at high speed. In FIG. 9A, the spring 71 is in its fully preloaded position. The amount of preload and the size of the spring are calculated to produce an appropriate apogee height for spring-ejection of the secondary penetrometer. Two restraint cables 75 made of steel wire with loops on either end are attached to the outer shell, looping around fasteners or pins. The opposite end of the wire cable loops around the dowel pin 73a, which is attached to the release slug 73. Tension in these wires locks the penetrometer in place, preventing it from being inadvertently ejected. The release slug is normally lightly preloaded against the accelerometer mount, also to prevent inadvertent release. When the outer shell impacts the surface, very high G forces are experienced (approximately 900 G). In FIG. 9B, the release slug 73, which may be made of tungsten carbide (about twice the density of steel), experiences this deceleration, and is propelled downward. As the release slug is propelled downward, the wire loops are released from the dowel pin 73a, and the secondary penetrometer is no longer constrained, allowing it (rod 31 indicated) to be ejected from the outer shell by the released force of the preloaded spring, as shown in FIGS. 9C and 9D. As an additional safeguard, a remove-before-flight pin may be used to insure that the penetrometer is not accidentally ejected. Other release mechanisms may be used, such as motor actuated latches, solenoids, pin pullers, ball couplings and pyrotechnic charges.

FIGS. 10A-10D illustrate the use of trim tab features to control the fall of the outer shell under gravity and tilt angle to allow clearance of the secondary penetrometer upon ejection from the buried outer shell. FIG. 10A shows the secondary penetrometer as described with respect to FIG. 3, the rear portion of which forms the rear portion of the combined unit in FIG. 4. The trim tabs are shown as simple plates on the rear end of the penetrometer aft body. In FIG. 10B, the use of a Drag Tab on one lateral side while no tab is used on the opposite side generates additional air drag force on that side during initial descent which causes a slight rotation about the center of gravity. In FIG. 10C, the use of a Drag Side Tab with a Drag Top Tab generates a drag force against the ejection velocity of the penetrometer. In FIG. 10D, the use of a Drag Side Tab relative to a Drag Top Tag generates a drag force on the falling secondary penetrometer. It is found that a small angle of as little as 1.0 degrees would be sufficient to allow clearance of the secondary penetrometer. For a small angle of 5° or less, the error associated with deceleration and depth measurements due to the inclination angle is less than 0.5%.

The dual-impact penetrometer approach substantially reduces overall system risk associated with target accuracy, system design complexity, and accurate interpretation of deceleration measurements. The high-velocity (>30 m/s) penetrometer impact data will provide crude knowledge of the soil strength but will provide information about soil density, while the low-velocity (<10 m/s) penetrometer impact data will provide much more accurate knowledge of soil strength. The combined system can be integrated with other sensors (e.g. moisture sensor, pore pressure sensor) to acquire higher fidelity data of a soil site.

Modifications may be made to the dual-impact penetrometer approach as different circumstances from those of the preferred embodiment may require. The system can be deployed from a moving plane for real time landing zone trafficability assessment prior to the plane approach for landing. The slower penetrometer can be slowed down via other means (e.g. parachute). A man-portable sensor version can be deployed to rapidly assess soil surface conditions (e.g., from a vehicle towed launcher). A GPS controlled guidance system can be attached to provide increased accuracy of deployment.

It is to be understood that many modifications and variations may be devised given the above described principles of the invention. It is intended that all such modifications and variations be considered as within the spirit and scope of this invention, as defined in the following claims.

The invention claimed is:

1. An aerial-drop dual-impact penetrometer system comprising:
a primary penetrometer formed as an outer shell having an outer shell fore body, for primary impact into a target area of soil on the ground, connected to an outer shell aft body having a rear recess therein;
a secondary penetrometer formed with a narrow-width, secondary fore body, for secondary impact into an adjacent target area of soil on the ground, connected to a secondary aft body sleeve, wherein said secondary penetrometer is combined in a unit with said primary penetrometer by at least the secondary fore body being received in telescoping fashion within the rear recess of the outer shell aft body of said primary penetrometer; and
an ejection mechanism provided within the outer shell aft body of said primary penetrometer for ejecting said secondary penetrometer upwards from the primary impact area into the area to fall to the adjacent secondary impact area on the ground.

2. An aerial-drop dual-impact penetrometer system according to claim 1, wherein the secondary aft body sleeve of said secondary penetrometer is provided with stabilizer fins and trim tab drag features on a rear portion thereof which also form a rear portion to the outer shell that controls the descent and angle of impact of the combined unit.

3. An aerial-drop dual-impact penetrometer system according to claim 2, wherein the trim tab drag features are configured to ensure a small degree angle of inclination of the outer shell on primary impact so that ejection of said secondary penetrometer and secondary impact occurs more than 1 m away from the primary impact.

4. An aerial-drop dual-impact penetrometer system according to claim 1, wherein the secondary aft body sleeve of said secondary penetrometer has a hollow interior for containing an electronic assembly for the combined unit.

5. An aerial-drop dual-impact penetrometer system according to claim 4, wherein said electronic assembly includes an accelerometer for recording primary impact and secondary impact deceleration data of said primary penetrometer and said secondary penetrometer, respectively.

6. An aerial-drop dual-impact penetrometer system according to claim 5, wherein said primary penetrometer is designed for a high-velocity impact of greater than 30 m/s, and said secondary penetrometer is designed to be ejected by said ejection mechanism for a low-velocity impact of less than 10 m/s, and both penetrometers provide deceleration data via the accelerometer for the target soil area on the ground.

7. An aerial-drop dual-impact penetrometer system according to claim 6, wherein the high-velocity penetrometer data are characterized by inertia for both granular and cohesive soils and enable estimation of strength values for granular soil and for cohesive soil, and the low-velocity penetrometer data are characterized by friction and soil strength mechanisms and enable identification of soil type as granular or cohesive and enable estimation of soil strength and correlated to standard measurement of a mobility model.

8. An aerial-drop dual-impact penetrometer system according to claim 6, wherein said secondary penetrometer has a secondary nose cone connected between the secondary fore body and the secondary aft body sleeve which is received in mating fashion in the rear recess of the outer shell aft body of said primary penetrometer.

9. An aerial-drop dual-impact penetrometer system according to claim 4, wherein said electronics assembly includes a satellite/GPS communications module for transmitting the deceleration data and GPS signals indicative of the impact area on the ground to a remote control center.

10. An aerial-drop dual-impact penetrometer system according to claim 1, wherein said ejection mechanism is a spring preload and release mechanism assembly for ejecting said secondary penetrometer into the air by spring force after impact of said primary penetrometer into the ground.

11. An aerial-drop dual-impact penetrometer system according to claim 10, wherein said secondary penetrometer is preloaded against a spring housed within the outer shell, and locked in place by restraint cables having opposite ends attached between the outer shell and a release slug, such that when the outer shell impacts the ground, very high G forces cause the release slug to be propelled in a downward direction and the ends of the restraint cable are released from the release slug, whereby said secondary penetrometer is ejected from the outer shell by the released force of the preloaded spring.

12. An aerial-drop dual-impact penetrometer system according to claim 1, wherein the secondary aft body sleeve of said secondary penetrometer contains an electronic assembly for the combined unit and a shock-isolation mechanism for reducing the electronics assembly from shock due to penetrometer impact on the ground.

13. An aerial-drop dual-impact penetrometer system according to claim 12, wherein the shock-isolation mechanism includes a light wave spring for isolating impact forces on the electronics assembly, and a skeleton structure for mounting electronic components of the electronics assembly in the secondary aft body sleeve.

14. An aerial-drop dual-impact penetrometer system according to claim 13, wherein the shock-isolation mechanism includes urethane foam or gel filled into a remaining volume of the secondary aft body sleeve once the skeleton structure with the electronics assembly is inserted therein.

15. An ejection mechanism for ejecting a secondary body from a primary body upon impact of the primary body into the ground, comprising:
the primary body being formed as an outer shell having a rear recess for receiving the secondary body therein in telescoping fashion;
the secondary body being preloaded against a spring housed within the outer shell, and locked in place by restraint cables having opposite ends attached between the outer shell and a release slug, such that when the outer shell impacts the ground, very high G forces cause the release slug to be propelled in a downward direction and the ends of the restraint cable are released from the release slug, whereby said secondary body is ejected from the outer shell by the released force of the preloaded spring.

16. A method of characterizing soil properties using an impact penetrometer comprising:
forming a primary penetrometer as an outer shell having a rear recess for receiving a secondary penetrometer therein in telescoping fashion;
enabling the primary penetrometer to have a primary impact into a target area of soil on the ground,
enabling the secondary penetrometer to be ejected into the air from the primary penetrometer after the primary impact in order to have a secondary impact into an adjacent target area of soil on the ground, and
measuring primary impact and secondary impact deceleration data of the primary penetrometer and the secondary penetrometer, respectively, with an accelerometer, and recording the deceleration data for analysis for characterizing soil properties.

17. A method of characterizing soil properties according to claim 16, wherein the primary penetrometer is designed for a high-velocity impact of greater than 30 m/s, and the secondary penetrometer is designed to be ejected for a low-velocity impact of less than 10 m/s, and both penetrometers are enabled to provide deceleration data via the accelerometer for the target soil area on the ground.

18. A method of characterizing soil properties according to claim 17, wherein the high-velocity penetrometer data are characterized by inertia for both granular and cohesive soils and enable estimation of strength values for granular soil and for cohesive soil, and the low-velocity penetrometer data are characterized by friction and soil strength mechanisms and enable identification of soil type as granular or cohesive and enable estimation of soil strength and correlated to standard measurement of a mobility model.

19. A method of characterizing soil properties according to claim 16, wherein the primary penetrometer is designed with trim tab drag features to ensure a small degree angle of inclination of the outer shell on primary impact so that ejection of the secondary penetrometer and secondary impact occurs more than 1 m away from the primary impact.

20. A method of characterizing soil properties according to claim 16, wherein the primary penetrometer is designed to be dropped in free fall from an unmanned aerial vehicle in remote terrain to be characterized for vehicle or robotic motility.

* * * * *